United States Patent [19]
Bufalini

[11] Patent Number: 5,707,359
[45] Date of Patent: Jan. 13, 1998

[54] EXPANDING TROCAR ASSEMBLY

[76] Inventor: Bruno Bufalini, 171 Hoover Dr., Cresskill, N.J. 07626

[21] Appl. No.: 557,490

[22] Filed: Nov. 14, 1995

[51] Int. Cl.$^6$ .................................................. A61M 29/00
[52] U.S. Cl. .......................... 604/104; 604/49; 604/167; 604/264; 6069/198; 6069/200
[58] Field of Search ...................... 604/49, 51, 93, 604/104–109, 167, 169, 236, 237, 248, 256, 264, 288; 606/198, 200; 600/201, 203

[56] References Cited

U.S. PATENT DOCUMENTS

| | | | |
|---|---|---|---|
| 4,692,139 | 9/1987 | Stiles | 604/109 |
| 4,716,901 | 1/1988 | Jackson et al. | |
| 4,807,625 | 2/1989 | Singleton . | |
| 4,997,435 | 3/1991 | Demeter | 604/104 |
| 5,011,488 | 4/1991 | Ginsburg | 604/104 |
| 5,176,687 | 1/1993 | Hasson et al. . | |
| 5,190,561 | 3/1993 | Graber . | |
| 5,192,298 | 3/1993 | Smith et al. . | |
| 5,195,506 | 3/1993 | Hulfish | 606/198 |
| 5,195,507 | 3/1993 | Bilweis . | |
| 5,226,426 | 7/1993 | Yoon | 604/169 |
| 5,263,937 | 11/1993 | Shipp . | |
| 5,279,548 | 1/1994 | Essig et al. . | |
| 5,312,417 | 5/1994 | Wilk | 604/264 |
| 5,330,497 | 7/1994 | Freitas et al. . | |
| 5,334,164 | 8/1994 | Guy et al. | 604/248 |
| 5,339,803 | 8/1994 | Mayzels et al. | 604/105 |
| 5,350,364 | 9/1994 | Stephens et al. | 604/256 |
| 5,509,900 | 4/1996 | Krikman | 604/104 |
| 5,554,124 | 9/1996 | Alvarado | 604/167 |

*Primary Examiner*—Michael Powell Buiz
*Assistant Examiner*—Bhisma Mehta

[57] ABSTRACT

An expandable trocar assembly including a trocar hilt secured to an inner sheath, wherein the inner sheath has an expandable distal end. The assembly further includes an outer sheath slidable positioned on the inner sheath, the outer sheath being movable to selectively cover and restrain the expandable distal end of the inner sheath.

12 Claims, 5 Drawing Sheets

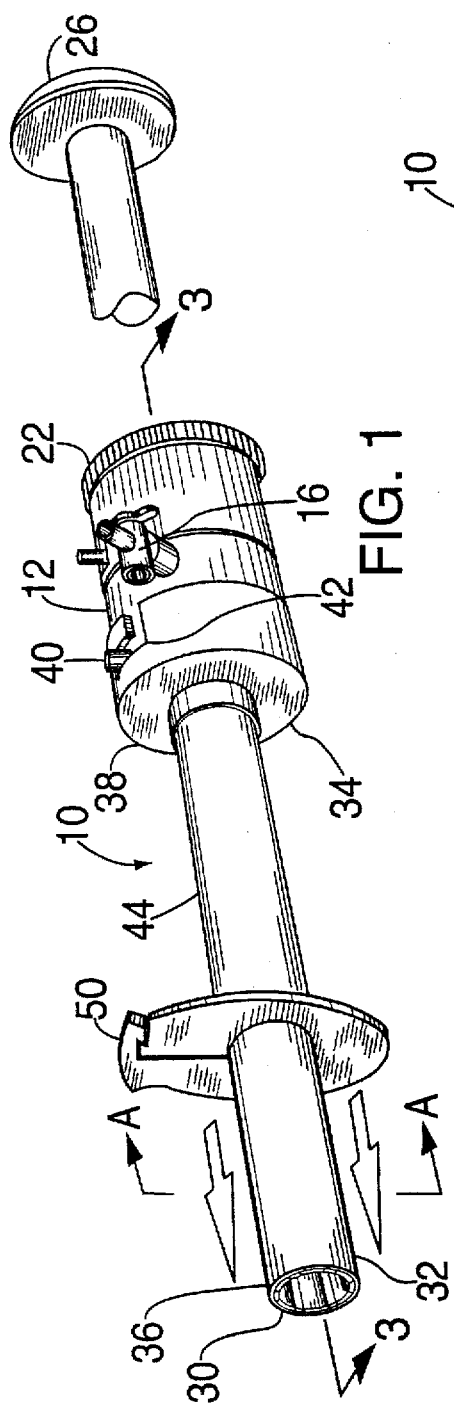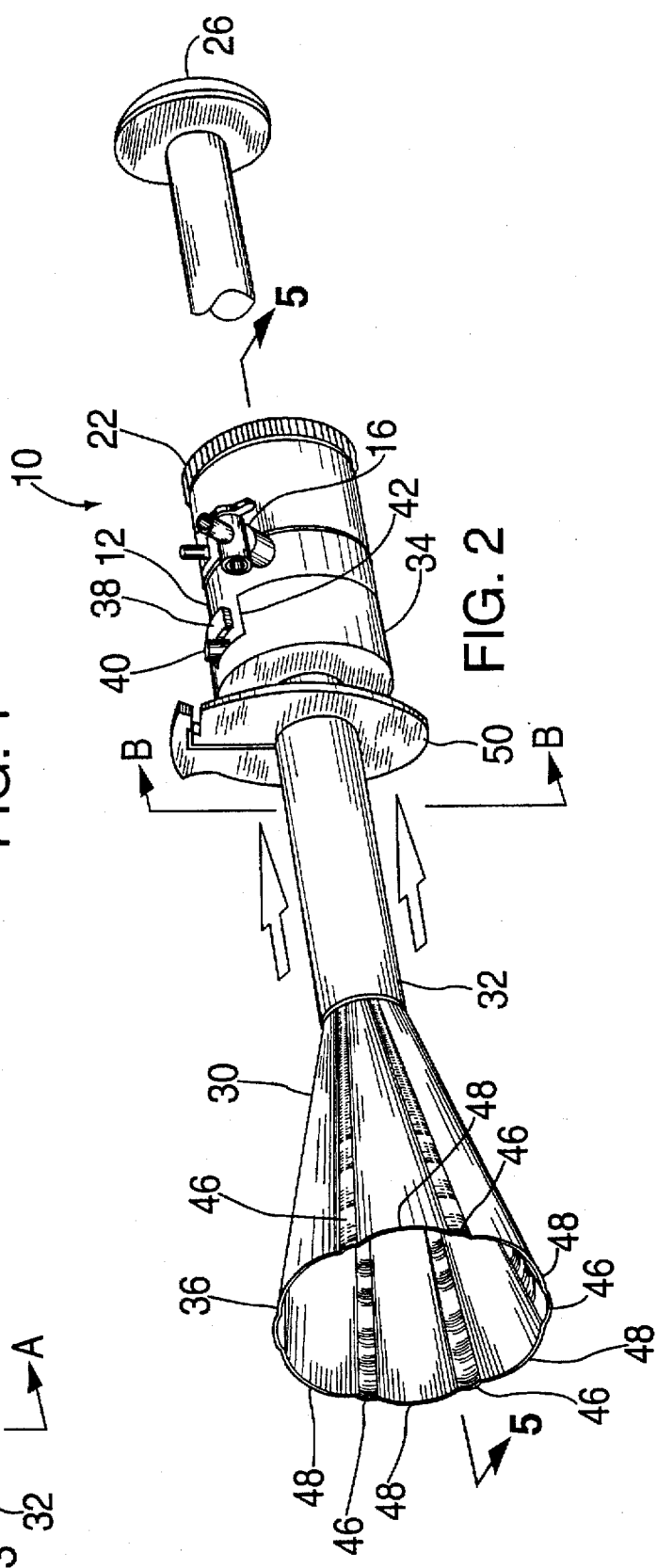

EXPANDING TROCAR ASSEMBLY

BACKGROUND OF THE INVENTION

1. Field of the Invention

The invention relates to surgical instruments. More particularly, the invention relates to expandable trocar assemblies used for the removal of tissue or organs from a surgical cavity.

2. Background of the Invention

During laparoscopic surgery it is often necessary to remove tissue or organs from a surgical cavity through small incisions. While removing the specimen, it is necessary to avoid contact between the organ, or tissue, and the walls of the incision. Additionally, it may be necessary to compress the organs or tissues to allow their passage through the small incisions.

Trocar assemblies for laparoscopic surgery are sized according to the inner diameter of the trocar sheath and usually range in size from 5 mm to 18 mm, or even greater if desired. There are numerous different trocars produced, by different manufacturers, while some are totally disposable, others are totally nondisposable instruments. Inexpensive trocar assemblies are also available, but these usually lack insufflation valves and/or inner flapper valves.

The variety of sizes are necessary to allow the insertion of different size instruments permitting extraction of specimens from the body cavity. Specimens to be extracted may include a gallbladder containing numerous small stones or a few large stones, an ovary, a lymph node, or some other tissue or organ. As stated previously, the specimen will often have a larger diameter than the trocar sheath through which it must be extracted. In such instances, various maneuvers must be used to extract the specimen. This, however, can result in the specimen lodging within the abdominal cavity with the ensuing danger of tearing or rupturing the tissue during forced extraction.

Whether the specimen is torn, damaged, or successfully severed, special care must be taken because the infected or cancerous tissue will be dragged through the abdominal wall incision and possibly contaminate the incision, or spread the cancer cells to the incision.

Intra-abdominal tissue collection devices have been developed to reduce the possibility of contamination. These devices include various types of plastic pouches. Even these, however, must be removed from the abdominal cavity where contamination may occur. Additionally, expandable trocar assemblies have been developed. For example, U.S. Pat. No. 5,312,417 to Wilk discloses a "Laparoscopic Cannula Assembly and Associated Method". The assembly utilizes an expandable web to receive a plurality of organs during laparoscopic surgery. The web is exposed for expansion by pushing an actuator ring toward the distal end of the assembly. Since the operating area in which the web must work is very small, the movement of the web necessary to permit its expansion may cause complications.

While the prior art discloses a variety of methods and apparatuses for performing laparoscopic surgery, the prior art devices have safety and functional shortcomings. The present invention overcomes the shortcomings of the prior art devices by providing a safe and convenient trocar assembly for performing laparoscopic surgery.

SUMMARY OF THE INVENTION

It is, therefore, an object of the present invention to provide a surgical tool facilitating the removal of specimens from a body cavity.

A further object of the present invention is the provision of an inexpensive trocar assembly which is partially or totally disposable.

It is also an object of the present invention to provide a reliable, safe and convenient expandable trocar assembly.

These and other objects are achieved by the present invention, which provides an expandable trocar assembly including a trocar housing secured to an inner sheath, wherein the inner sheath has an expandable distal end. The assembly further includes an outer sheath slidable positioned on the inner sheath, the outer sheath being movable to selectively cover and restrain the expandable distal end of the inner sheath.

Other objects, advantages and salient features of the invention will become apparent from the following detailed description, which taken in conjunction with the annexed drawings, discloses a preferred, but non-limiting, embodiment of the subject invention.

BRIEF DESCRIPTION OF THE DRAWINGS

FIG. 1 is a perspective view of the trocar assembly with the expanding distal end of the inner sheath covered.

FIG. 2 is a perspective view of the trocar assembly with the expanding distal end of the inner sheath exposed.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

Figure 3:
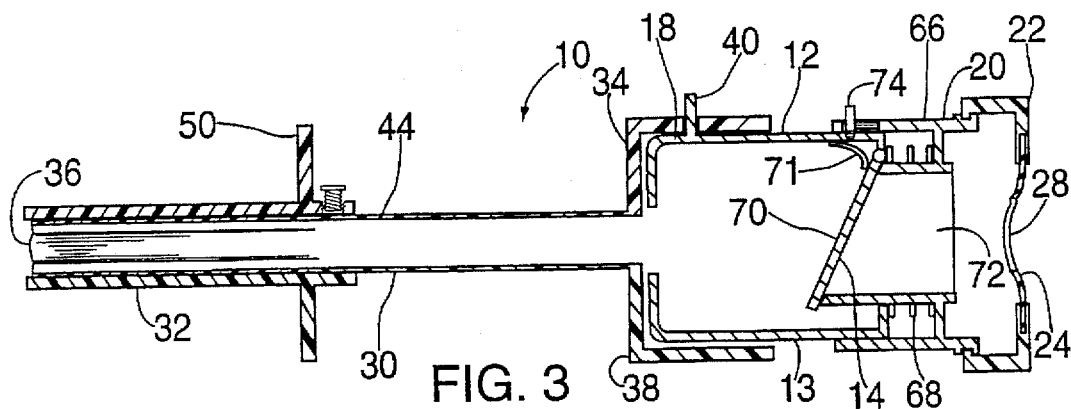
FIG. 3 is a cross-sectional view of the trocar assembly with the distal end of the inner sheath covered and the flapper valve closed.
Figure 4:
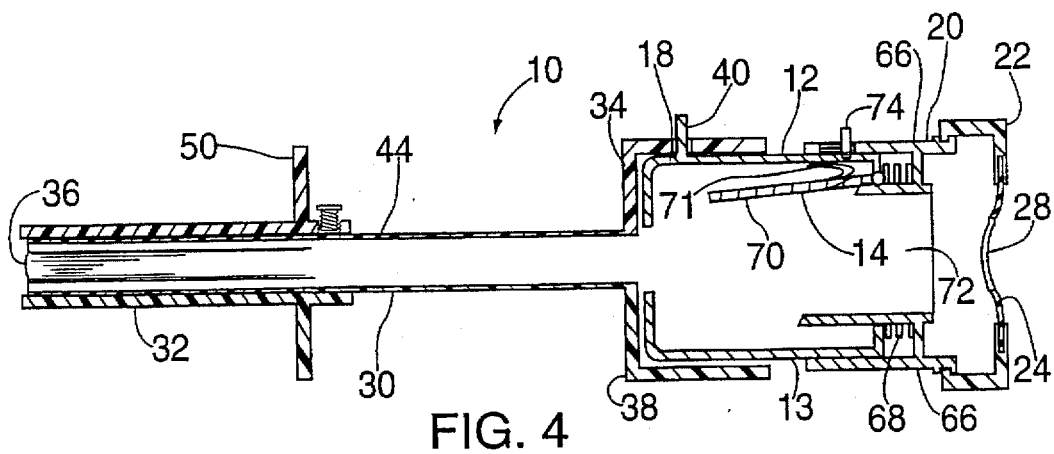
FIG. 4 is a cross-sectional view of the trocar assembly with the distal end of the inner sheath covered and the flapper valve opened.
Figure 5:
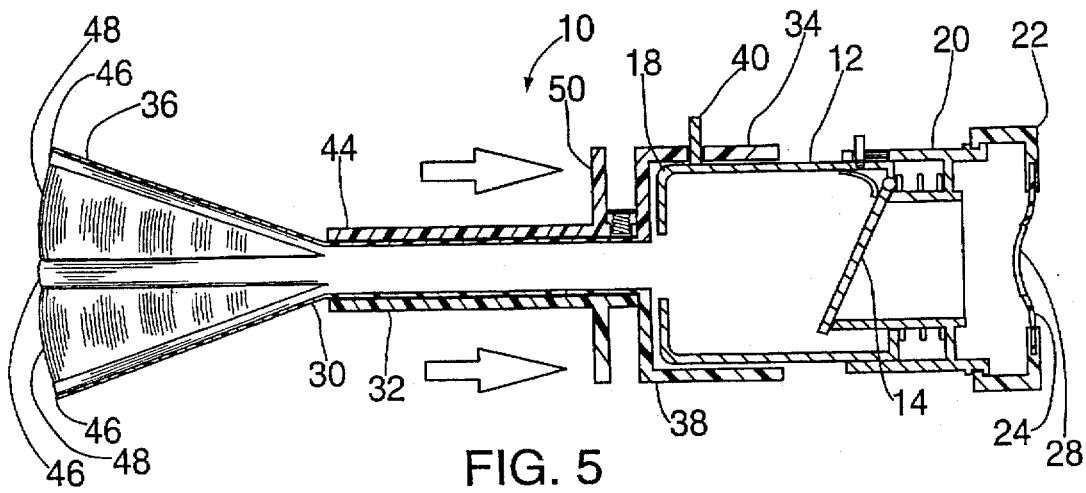
FIG. 5 is a cross-sectional view of the trocar assembly with the distal end of the inner sheath exposed.
Figure 6:
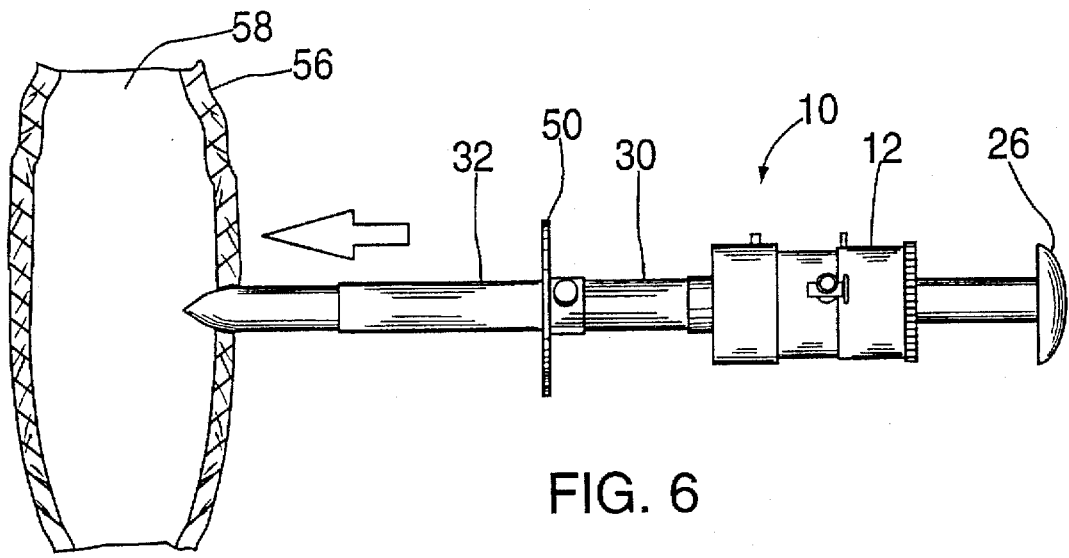
FIG. 6 is a perspective view of the trocar being inserted through the abdominal wall.
Figure 7:
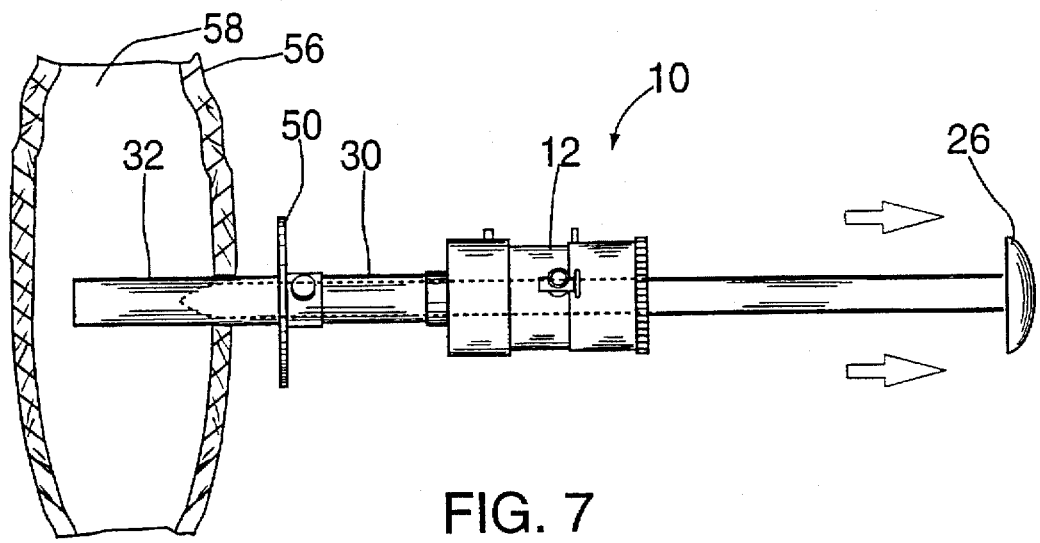
FIG. 7 is a perspective view of the inner sheath and outer sheath in position within the abdominal cavity.
Figure 8:
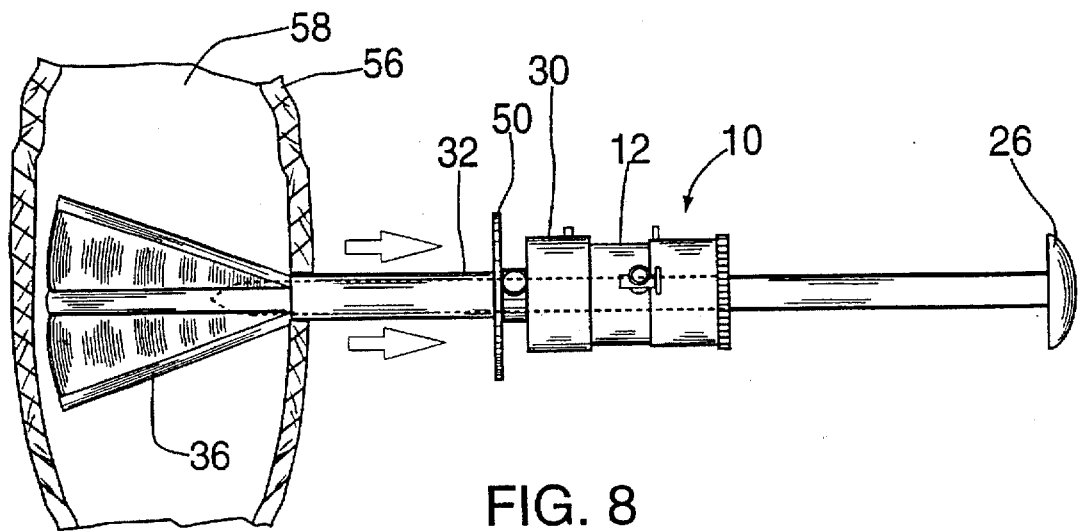
FIG. 8 is a perspective view of the distal end of the inner sheath expanded within the abdominal cavity.
Figure 9:
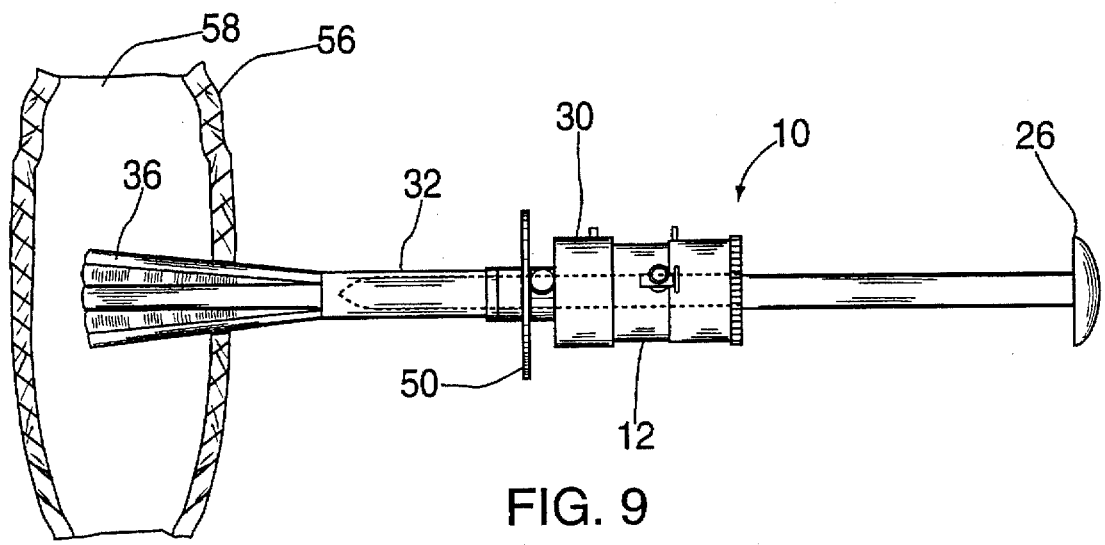
FIG. 9 and 10 show the assembly being removed from the abdominal cavity.
Figure 10:
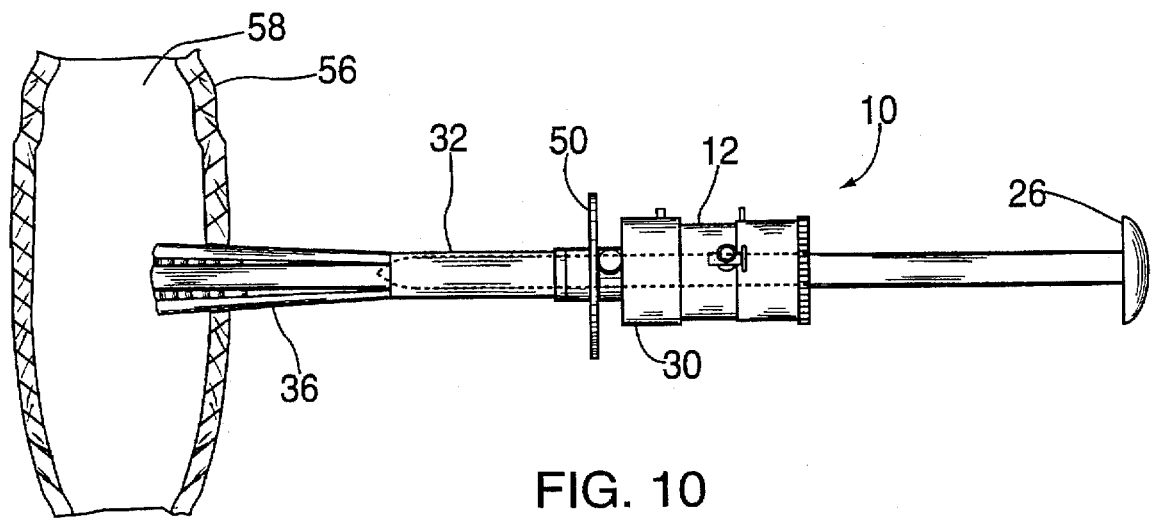
Figure 11:
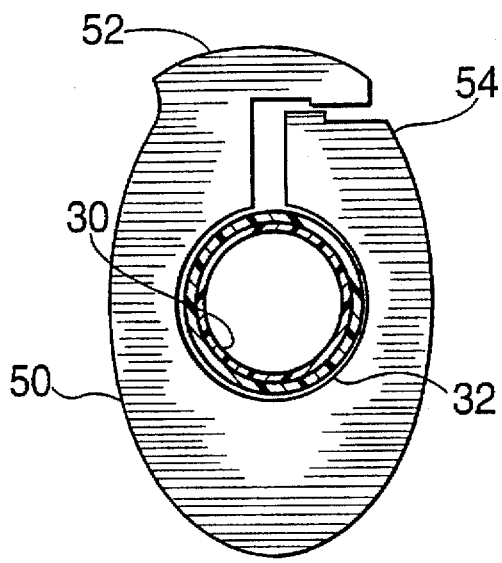
FIG. 11 is a cross-sectional view along the line A—A of FIG. 1.
Figure 12:
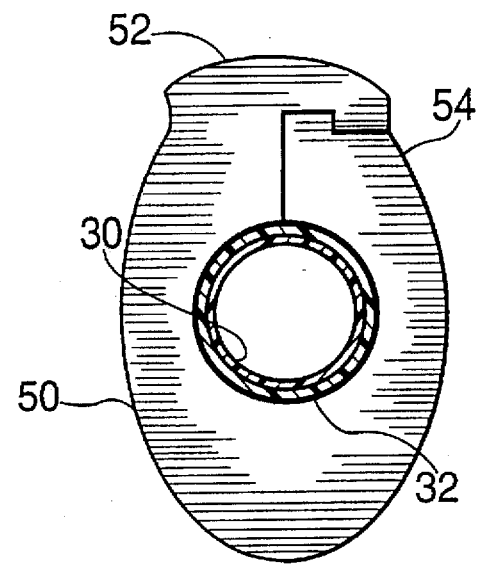
FIG. 12 is a cross-sectional view along the line B—B in FIG. 2.

With reference to FIG. 1, an expandable trocar assembly 10 is provided. The trocar assembly 10 includes hilt 12 having a main body 13 containing a flapper valve assembly 14 and an insufflating petcock 16, which are used in the removal of specimens from a patient's body. The hilt 12 includes a distal end 18 and a proximal end 20. As shown in FIGS. 3 and 4, the flapper valve assembly 14 includes a cylindrical support 66 located at the proximal end 20 of hilt 12. The cylindrical support 66 is resiliently biased by spring 68 against the main body 13 of the hilt 12. The flapper valve assembly 14 further includes a flapper 70 pivotally mounted to the main body 13 and resiliently biased by spring 71 away from the main body 13 to cover an opening 72 in the cylindrical support 66. The flapper valve assembly 14 is constructed to permit the cylindrical support 66 to be pushed proximally and force the valve 70 away from the opening 72. When the pressure is released, the springs 68, 71 respectively force the cylindrical housing 66 and the flapper 70 back to their closed positions. Movement of the cylindrical support 66 is further controlled by a pin 74, which restrains proximal and distal movement of the cylindrical support 66.

While the hilt 12 is preferably made of stainless steel, it can be made of plastic without departing from the spirit of the present invention. When the hilt 12 is made of plastic, the entire assembly can be inexpensively manufactured permitting disposal of the entire trocar assembly.

A disposable cap 22 is releasable secured to the proximal end 20 of the hilt 12. The cap 22 includes a central opening 24 through which a trocar 26, or other instrument, may pass. The central opening 24 is covered by a penetrably membrane 28 which maintains the sterility of the assembly 10 prior to insertion and permits the trocar 26 to pass through the hilt 12 when the assembly 10 is in use.

An inner sheath 30 is releasable secured to the distal end 18 of the hilt 12 and is covered by an outer sheath 32. The inner sheath 30 and outer sheath 32 are made of inexpensive plastics and are removably secured to disposable or non-disposable hilt 12. As a result, the sheaths may be readily replaced permitting the simple and inexpensive application of sterile sheaths. Additionally, the sheaths may be made in a variety of sizes, all of which fit the same non-disposable hilt 12. The combination of the disposable sheaths with the non-disposable metal hilt 12 results in a trocar assembly 10 which is inexpensive, readily replaceable, sterile, and easily converted for different incision sizes. When the hilt 12 is made of plastic, the entire assembly 10 may be disposed of after each use without undue expense.

The inner sheath 30 includes a proximal end 34 and a distal end 36. The proximal end 34 includes a coupling member 38 engaging a connecting pin 40 on the hilt 12 to releasably secure the inner sheath 30 to the hilt 12. The coupling member 38 is cylindrically shaped to fit around the hilt 12 and is provided with a L-shaped cut out 42 which engages the connecting pin 40 to securely hold the inner sheath 30 in position. Specifically, the coupling member 38 is positioned on the hilt 12 to permit the connecting pin 40 to pass within the L-shaped cut out 42. The inner sheath 30 is then rotated to securely engage the inner sheath 30 and the hilt 12.

The coupling member 38 leads to a central cylindrical shaft portion 44. The distal end 36 of the inner sheath 30 is slit into four or five ribs 46. The ribs 46 maybe reinforced with fiberglass and preshaped to expand into a funnel shape when they are not restrained, for example, by the outer sheath 32 as will be discussed in more detail below. The ribs 46 are interconnected by plastic webbing members 48. The webbing controls the spacing between the ribs 46 when the distal end 36 of the inner sheath 30 is expanded.

Figure 13:
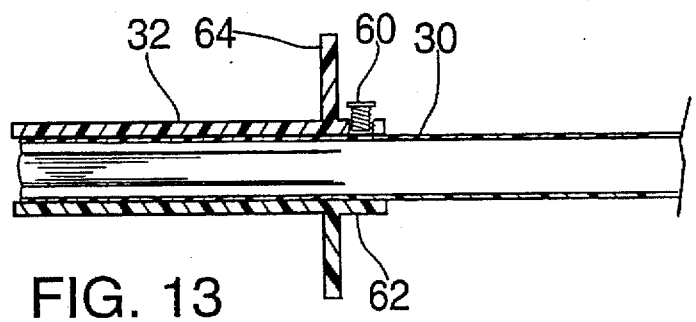
FIGS. 13 and 14 are cross-sectional views of an alternate embodiment of the present invention.
Figure 14:
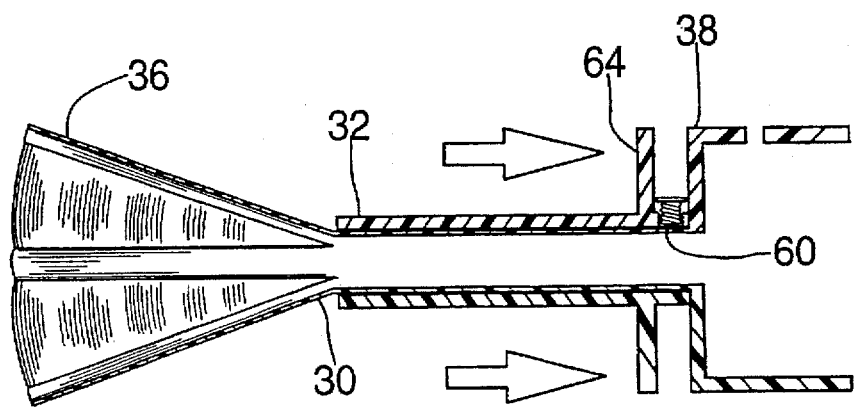

Prior to use, the expandable distal end 36 of the inner sheath 30 is stored within an outer sheath 32. The outer sheath 32 is approximately one-half the length of the inner sheath 30 and is slidable along the surface of the inner sheath. As will be discussed in more detail below, the outer sheath 32 slides forward and backward along the length of the inner sheath 30 to restrain or release the expanding distal end 36 of the inner sheath 30. The outer sheath 32 is provided with a locking flange 50 for securely holding the outer sheath 32 on the inner sheath 30. The locking flange 50 is integrally formed with the outer sheath 32 and includes a pair of interlocking elements 52, 54 which form a compression fit about the inner sheath 30 when the interlocking elements 52, 54 are engaged. The locking flange 50 also acts as a handle permitting a user to move the outer sheath 32 along the inner sheath 30. As shown in FIGS. 13 and 14, the locking flange 50 could be replaced by a set screw 60 mounted on the distal end 62 of the outer sheath 32. The set screw 60 would then be tightened or released to permit movement of the outer sheath 32. A handle 64 could also be provided to permit movement of the outer sheath 32.

Use of the trocar assembly is shown in FIGS. 6 to 10. The trocar 26 is first passed through the hilt 12 and the inner sheath 30. The trocar 26 is then moved through the abdominal wall 56, creating a cavity through which the inner sheath 30 and the outer sheath 32 may pass. The assembly 10 is inserted through the abdominal wall 56 while the outer sheath 32 is in its forward position covering the distal end 36 of the inner sheath 30; that is, the expandable ribs 46 of the inner sheath 30 are compressed within the outer sheath 32.

The inner sheath 30 and the outer sheath 32 are then inserted by the physician an appropriate distance into the abdominal cavity 58. Once the inner sheath 30 and the outer sheath 32 have been inserted, the locking flange 50 is released. Further pressure by the physician allows the outer sheath 32 to slide proximally along the inner sheath 30, thereby exposing the distal end 36 of the inner sheath 30 and permitting the ribs 46 to expand to their funnel shape. The surgical procedure is then carried out in the usual fashion until the end of the procedure at which time the specimen has been severed from the patient's body. Once the surgical procedure is completed the trocar assembly 10 is withdrawn from the body, with the ribs 46 and plastic members 48 enclosing the specimen as it passes through the incision.

The distal end 36 of the inner sheath 30 could be provided with purse-string ligature (not shown) permitting controlled closure of the ribs around a specimen. Specifically, the purse-string ligature would be secured to the outer ends of the ribs to permit the ribs to be drawn together when the ligature is pulled in a direction away from the ribs.

While various preferred embodiments have been shown and described, it will be understood that there is no intent to limit the invention by such disclosure, but rather, is intended to cover all modifications and alternate constructions falling within the spirit and scope of the invention as defined in the appended claims.

I claim:

1. An expandable trocar assembly, comprising: a trocar hilt secured to an inner sheath, the inner sheath including an expandable distal end, the distal end being formed of a plurality of ribs which assume a funnel shape when unrestrained;

an outer sheath slidably positioned on the inner sheath for movement on the inner sheath while the trocar hilt is secured to the inner sheath, the outer sheath being movable to selectively cover and restrain the expandable distal end of the inner sheath during insertion, the trocar hilt including a main body containing a flapper valve positioned at a proximal end of the main body and resiliently biased to a closed position, and wherein the flapper valve includes a cylindrical support located at the proximal end of the main body and a flapper pivotally supported by the cylindrical support within the main body, and wherein movement of the cylindrical support causes the flapper to move to an opened position.

2. The trocar assembly according to claim 1, wherein the inner sheath is releasable secured to the trocar hilt.

3. The trocar assembly according to claim 1, wherein the inner sheath and the outer sheath are made of plastic.

4. The trocar assembly according to claim 1, wherein the ribs are connected by webbing members.

5. The trocar assembly according to claim 1, wherein the outer sheath is provided with an integral locking flange for securing the outer sheath to the inner sheath.

6. The trocar assembly according to claim 1, wherein axial movement or the cylindrical support causes the flapper to move to an opened position.

7. A laparoscopy method, comprising the steps of: inserting a trocar assembly in through the abdominal wall of a patient, the trocar assembly including a trocar hilt secured to an inner sheath, the inner sheath including an expandable distal end formed of a plurality of ribs which assume a funnel shape when unrestrained, and an outer sheath slidably positioned on the inner sheath for movement on the inner sheath while the trocar hilt is secured to the inner sheath, the outer sheath covering and restraining the expandable distal end of the inner sheath;

drawing the outer sheath away from the expandable distal end of the inner sheath and permitting the plurality of ribs to assume the unrestrained funnel shape;

severing a tissue sample; and withdrawing the tissue sample and the trocar assembly from the patient, the trocar hilt including a main body containing a flapper valve positioned at a proximal end of the main body and resiliently biased to a closed position, and wherein the flapper valve includes a cylindrical support located at the proximal end of the main body and a flapper pivotally supported by the cylindrical support within the main body, and wherein movement of the cylindrical support causes the flapper to move to an opened positioned.

8. The method according to claim 7, wherein the inner sheath is releasable secured to the trocar hilt.

9. The method according to claim 7, wherein the inner sheath and the outer sheath are made of plastic.

10. The method according to claim 7, wherein the ribs are connected by webbing members.

11. The method according to claim 7, wherein the outer sheath is provided with an integral locking flange for securing the outer sheath to the inner sheath.

12. The method according to claim 7, wherein axial movement of the cylindrical support causes the flapper to move to an opened position.

* * * * *